(12) United States Patent
Tawada

(10) Patent No.: US 8,646,912 B2
(45) Date of Patent: Feb. 11, 2014

(54) FUNDUS PHOTOGRAPHING APPARATUS

(75) Inventor: Akira Tawada, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 176 days.

(21) Appl. No.: 12/801,913

(22) Filed: Jul. 1, 2010

(65) Prior Publication Data

US 2011/0001929 A1  Jan. 6, 2011

(30) Foreign Application Priority Data

Jul. 3, 2009 (JP) ................................ 2009-158825

(51) Int. Cl.
*A61B 3/14* (2006.01)
*A61B 3/10* (2006.01)

(52) U.S. Cl.
USPC .......................... 351/206; 351/208; 351/211

(58) Field of Classification Search
USPC ................................................ 351/206, 208
See application file for complete search history.

(56) References Cited

U.S. PATENT DOCUMENTS

| 6,325,511 | B1 * | 12/2001 | Mizuochi ..................... 351/206 |
| 6,574,432 | B2 | 6/2003 | Nanjyo |
| 7,429,107 | B2 | 9/2008 | Mizuochi |
| 7,837,329 | B2 * | 11/2010 | Yoshino et al. ............... 351/206 |
| 2011/0267583 | A1 * | 11/2011 | Hayashi ........................ 351/206 |
| 2012/0038886 | A1 * | 2/2012 | Dobashi et al. ............... 351/208 |
| 2012/0044456 | A1 * | 2/2012 | Hayashi ........................ 351/206 |

FOREIGN PATENT DOCUMENTS

| JP | A-09-070388 | 3/1997 |
| JP | A-2000-157493 | 6/2000 |
| JP | A-2000-262477 | 9/2000 |
| JP | A-2001-258850 | 9/2001 |
| JP | A-2004-081255 | 3/2004 |
| JP | A-2005-095450 | 4/2005 |
| JP | A-2006-167068 | 6/2006 |

* cited by examiner

*Primary Examiner* — Jordan Schwartz
(74) *Attorney, Agent, or Firm* — Oliff PLC

(57) ABSTRACT

A fundus photographing apparatus has an optical system including a movable focusing lens and photographing a fundus, an optical system photo-receiving by a first image pickup element a target from an alignment target projection optical system and detect an alignment state of the photographing optical system with respect to an eye based on a result by the first element, a detection optical system photo-receiving by a second image pickup element a target from a focus target projection optical system and detect a focus state adjusted by moving the lens based on a photo-receiving result by the second element, a unit controlling a light source to successively emit flash light at predetermined intervals in a predetermined period to perform fluorescent photographing, and a unit controlling movement of the photographing optical system with respect to the eye based on a result by the alignment detection optical system during the predetermined period.

10 Claims, 3 Drawing Sheets

FUNDUS PHOTOGRAPHING APPARATUS

BACKGROUND OF THE INVENTION

1. Field of the Invention

The present invention relates to a fundus photographing apparatus arranged to photograph a fundus of an examinee's eye.

2. Description of Related Art

Conventionally, for a fundus photographing apparatus arranged to photograph a fundus of an examinee's eye, there is known a fundus photographing apparatus arranged to perform alignment or fundus observation by photo-receiving infrared light for observation from an observation illumination optical system by a fundus observation optical system and displaying a fundus image formed by the infrared light on a monitor. In addition, there is known a non-mydriasis type fundus camera arranged to perform fundus photographing by photo-receiving visible light for photographing from a photographing illumination optical system. For this kind of non-mydriasis type fundus camera, there is proposed a fundus camera that includes an exciter filter for visible fluorescent photographing and a barrier filter arranged to transmit fluorescent light and infrared light that are insertably and removably provided, and thus has the function of performing fluorescent photographing simply (see Japanese Patent Application Laid-open Publication No. 2001-258850 corresponding to US 2003/0068164 A1).

In the fundus camera that is proposed in Japanese Patent Application Laid-open Publication No. 2001-258850, alignment during fluorescent photographing is performed while an infrared image displayed on a monitor is observed. In order to obtain a detailed temporal change in the early stage of introduction of a fluorescent agent, fluorescent photographing is often performed successively at given intervals (e.g., at one-second intervals), and it is difficult to perform proper alignment when photographing is performed at such short intervals. In addition, it is desired to successively check a temporal change of a fluorescent image obtained by performing successive fluorescent photographing.

SUMMARY OF THE INVENTION

An object of the invention is to overcome the problems described above and to provide a fundus photographing apparatus capable of easily obtaining a change of fluorescent light during fluorescent photographing and favorably performing successive fluorescent photographing.

To achieve the objects and in accordance with the purpose of the present invention, a fundus photographing apparatus arranged to perform fluorescent photographing by projecting flash light for fluorescent excitation onto an examinee's eye has a photographing optical system including a focusing lens movable in an optical axis direction and arranged to photograph a fundus of the eye illuminated by photographing illumination light, an alignment detection optical system arranged to photo-receive by a first image pickup element an alignment target projected onto the eye by an alignment target projection optical system and detect an alignment state of the photographing optical system with respect to the eye based on a photo-receiving result by the first image pickup element, a focus detection optical system arranged to photo-receive by a second image pickup element a focus target projected onto the fundus by a focus target projection optical system and detect a focus state of the fundus adjusted by movement of the focusing lens based on a photo-receiving result by the second image pickup element, a light emission control unit arranged to control a light source to perform successive light emission of the flash light for fluorescent excitation at predetermined time intervals in a predetermined period in order to perform fluorescent photographing, and a movement control unit arranged to perform movement control of the photographing optical system with respect to the eye based on a detection result obtained by the alignment detection optical system during the predetermined period of the successive light emission by the light emission control unit.

Additional objects and advantages of the invention are set forth in the description which follows, are obvious from the description, or may be learned by practicing the invention. The objects and advantages of the invention may be realized and attained by the fundus photographing apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
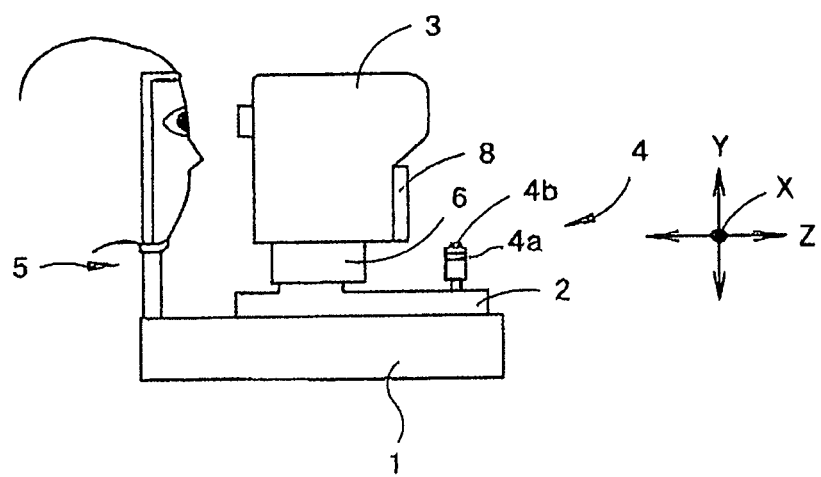
FIG. 1 is an external view showing a schematic configuration of a fundus photographing apparatus (a fundus camera) according to a preferred embodiment of the present invention.

A detailed description of one preferred embodiment of a fundus photographing apparatus embodied by the present invention is provided below with reference to the accompanying drawings. FIG. 1 is an external view showing a schematic configuration of the fundus photographing apparatus (a fundus camera) according to the preferred embodiment of the present invention. The fundus camera includes a base 1, a mobile base 2 that is movable in a right and left direction (an X direction) and in a back and forth direction (a Z direction) with respect to the base 1, a photographing unit (an apparatus main body) 3 that is movable in three-dimensional directions with respect to the mobile base 2 and houses an optical system to be described later, and a face supporting unit 5 that is fixed to the base 1 and is arranged to support the face of an examinee. The photographing unit 3 is moved in the X direction, an up and down direction (a Y direction), and the Z direction with respect to an examinee's eye E by an XYZ driving unit 6 provided to the mobile base 2. The mobile base 2 is moved in the X and Z directions on the base 1 by operation of a joystick 4. Operation of a rotation knob 4a drives the XYZ driving unit 6 and moves the photographing unit 3 in the Y direction. On an examiner's side of the photographing unit 3, a monitor 8 arranged to display a fundus observation image, a fundus photographing image, an anterior-segment observation image, and other images is provided.

Figure 2:
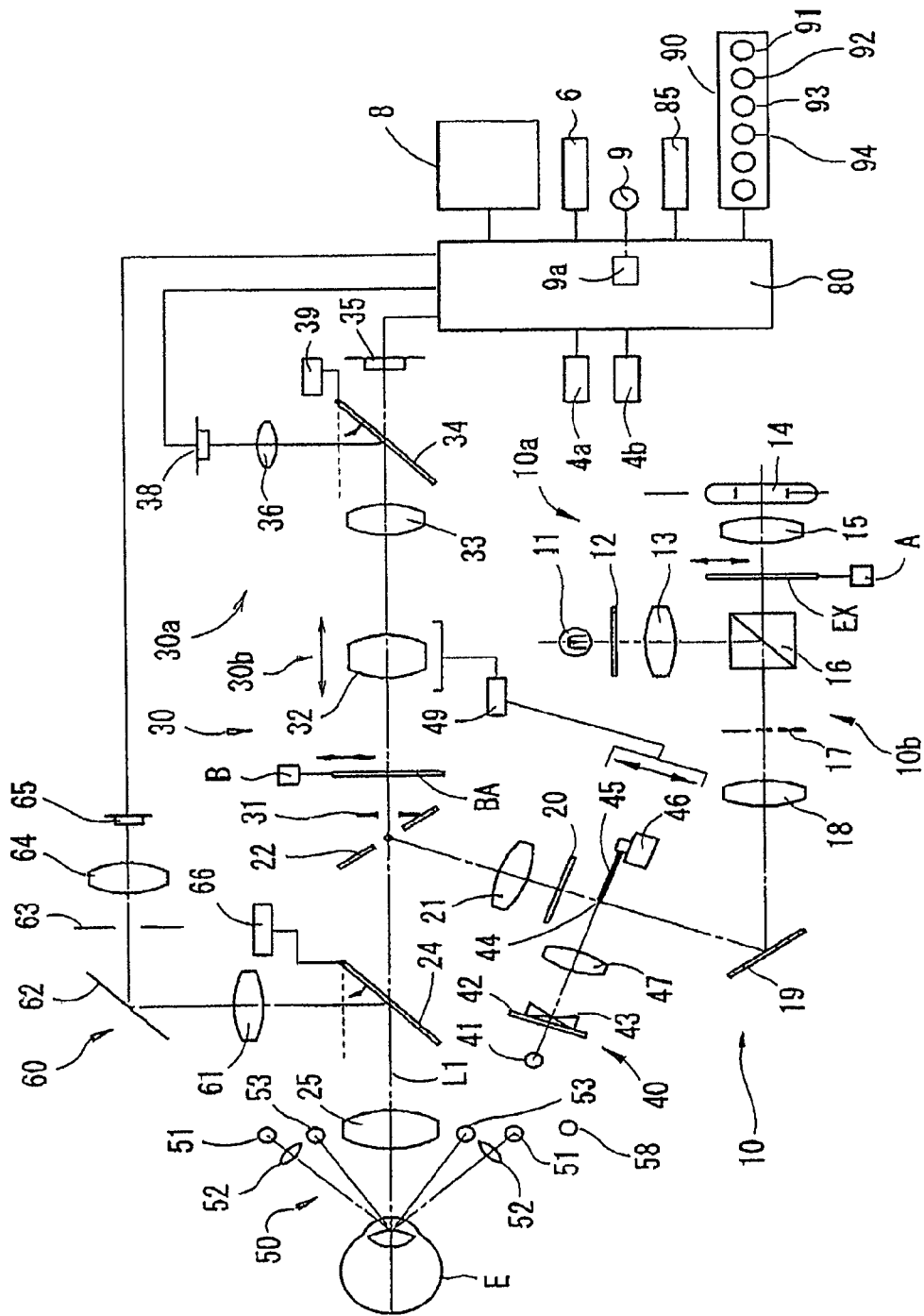
FIG. 2 is a schematic view of an optical system of the fundus camera.

FIG. 2 is a schematic view of an optical system of the fundus camera according to the preferred embodiment of the present invention. The optical system is roughly constituted of an illumination optical system 10 (an observation illumination optical system 10a, a photographing illumination optical system 10b), a fundus observation and photographing optical system 30 (a fundus observation optical system 30a, a fundus photographing optical system 30b), a focus target projection optical system 40, an alignment target projection optical system 50, and an anterior-segment observation optical system 60.

Illumination Optical System 10

The observation illumination optical system 10a of the illumination optical system 10 includes a light source 11 such as a halogen lamp, an infrared filter 12 arranged to transmit near infrared light having a wavelength of 750 nm or more, a condenser lens 13, a dichroic mirror 16 disposed between the condenser lens 13 and a ring slit 17, the ring slit 17 having a ring-shaped opening, a relay lens 18, a mirror 19, a black dot plate 20 having a black dot at the center, a relay lens 21, an apertured mirror 22, and an objective lens 25. The dichroic mirror 16 defining a wavelength selecting member has properties of reflecting infrared light and transmitting visible light.

The photographing illumination optical system 10b of the illumination optical system 10 includes a photographing light source 14 such as a flash lamp, a condenser lens 15, an exciter filter EX disposed so as to be inserted into and removed from an optical path by an inserting and removing mechanism A, and the optical system from the ring slit 17 to the objective lens 25. The exciter filter EX has a wavelength selecting property of making visible illumination light having a wavelength of about 450 nm to 520 nm into fluorescent excitation light, and is removed from the optical path during normal color photographing and inserted into the optical path during fluorescent photographing.

The exciter filter EX is disposed insertably and removably on the optical path between the light source 14 arranged to emit visible light and the wavelength selecting member 16 having a property of reflecting infrared light and transmitting visible light. Thus, infrared light from the observation illumination optical system 10a is prevented from being cut by the exciter filter EX during fluorescent photographing. If the exciter filter EX is provided with a property of transmitting fluorescent excitation light and infrared light from the observation illumination optical system 10a, the exciter filter EX may be disposed insertably and removably on an optical path between the light source 11 and the apertured mirror 22.

Fundus Observation and Photographing Optical System 30

The fundus observation optical system 30a of the fundus observation and photographing optical system 30 includes the objective lens 25, a photographing diaphragm 31 disposed in the vicinity of the aperture of the apertured mirror 22, a focusing lens 32 movable in an optical axis direction, an image forming lens 33, a pop-up mirror 34 that is inserted into and removed from an optical path by an inserting and removing mechanism 39 during fundus photographing, a relay lens 36 disposed on an optical path in a reflecting direction of the pop-up mirror 34, and a two-dimensional image pickup element 38 for observation having sensitivity to an infrared range. The photographing diaphragm 31 is disposed at a position substantially conjugate with a pupil of the eye E with respect to the objective lens 25. The focusing lens 32 is moved in the optical axis direction by a moving mechanism 49 including a motor.

The fundus photographing optical system 30b of the fundus observation and photographing optical system 30 shares the objective lens 25 and the optical system from the photographing diaphragm 31 to the image forming lens 33 with the fundus observation optical system 30a, and includes a barrier filter BA that is disposed so as to be inserted into and removed from an optical path by an inserting and removing mechanism B, and a two-dimensional image pickup element 35 for photographing having sensitivity to a visible range. The barrier filter BA has properties of transmitting fluorescent light that is excited by fluorescent excitation light and cutting infrared light and fluorescent excitation light from the illumination optical system 10, and is removed from the optical path during normal color photographing and inserted into the optical path during fluorescent photographing. The barrier filter BA may be disposed in the fundus photographing optical system 30b at a position that is not in the common optical path of the anterior-segment observation optical system 60 and the illumination optical system 10 and is in an optical path between the aperture mirror 22 and the image pickup element 35. Detailed descriptions of the anterior-segment observation optical system 60 are to be given later.

A dichroic mirror (a wavelength selective mirror) 24 defining an optical path dividing member is insertably and removably disposed obliquely between the objective lens 25 and the apertured mirror 22. The dichroic mirror 24 has properties of reflecting light within an infrared wavelength range (a center wavelength of 940 nm) including light from the alignment target projection optical system 50 and light from an anterior-segment illumination light source 58, and transmitting light within an infrared wavelength range of approximately 900 nm or less (a center wavelength of 880 nm) including light for fundus observation and light from the focus target projection optical system 40. During photographing, the dichroic mirror 24 is flipped up by an inserting and removing mechanism 66 so as to be removed from the optical path. A known mechanism such as a solenoid and a cam may be used for the inserting and removing mechanism 66.

Light emitted from the light source 11 for observation is made into infrared light by the infrared filter 12, passes through the condenser lens 13, and is reflected by the dichroic mirror 16 so as to illuminate the ring slit 17. The light transmitted through the ring slit 17 passes through the relay lens 18, the mirror 19, the black point plate 20, and the relay lens 21 to reach the apertured mirror 22. The light reflected from the apertured mirror 22 is transmitted through the dichroic mirror 24, is made to converge once in the vicinity of the pupil by the objective lens 25, and then diffuses to illuminate a fundus of the eye E. The light reflected from the fundus passes through the objective lens 25, the dichroic mirror 24, the aperture of the apertured mirror 22, the photographing diaphragm 31, the focusing lens 32, the image forming lens 33, the pop-up mirror 34, and the relay lens 36 to form an image of the fundus on the image pickup element 38.

By light emission of the light source 14, the fundus is illuminated with visible light. The light reflected from the fundus passes through the objective lens 25, the aperture of the apertured mirror 22, the photographing diaphragm 31, the focusing lens 32, and the image forming lens 33 to form an image of the fundus on the image pickup element 35. When the fundus camera is in a fluorescent photographing mode, light (fluorescent light) reflected from the fundus is transmitted through the barrier filter BA and forms an image of the fundus on the image pickup element 35.

Focus Target Projection Optical System 40

The focus target projection optical system 40 includes an infrared light source 41, a slit target plate 42, two deflection-angle prisms 43 attached to the slit target plate 42, a projection lens 47, and a spot mirror 44 that is disposed obliquely on the optical path of the illumination optical system 10. The spot mirror 44 is fixed to the end of a lever 45. The spot mirror 44 is normally disposed obliquely on the optical path and is removed from the optical path by rotation of the shaft of a rotary solenoid 46 during photographing. The spot mirror 44 is disposed at a position conjugate with the fundus. The light source 41, the slit target plate 42, the deflection-angle prisms 43, the projection lens 47, the spot mirror 44, and the lever 45 are moved in the optical axis direction in synchronization with the focusing lens 32 by a moving mechanism 49. Light from the light source 41 passes through the slit target plate 42, the deflection-angle prisms 43 and the projection lens 47, is reflected by the spot mirror 44, and passes through the relay lens 21, the apertured mirror 22, the dichroic mirror 24, and the objective lens 25 to be projected onto the fundus. When the fundus is out of focus, target images of the slit target plate 42 are separate, and when the fundus is in focus, the target images coincide.

The focus target images projected onto the fundus are picked with the fundus image by the image pickup element 38 for fundus observation.

Alignment Target Projection Optical System 50

The alignment target projection optical system 50 arranged to project target light for alignment includes first target projection optical systems having infrared light sources 51 and collimating lenses 52 and arranged laterally symmetrical with respect to a photographing optical axis L1, and second target projection optical systems having two infrared light sources 53, having optical axes forming an angle narrower than that of the first target projection optical systems, and arranged laterally symmetrical interposing a vertical plane which the optical axis L1 passes through. The first target projection optical systems project infinite targets onto a cornea of the eye E, and the second target projection optical systems project finite targets onto the cornea. The second target projection optical systems are disposed lower than the first target projection optical systems in order that the projected target light may not fall on the pupil.

Anterior-Segment Observation Optical System 60

Figure 3:
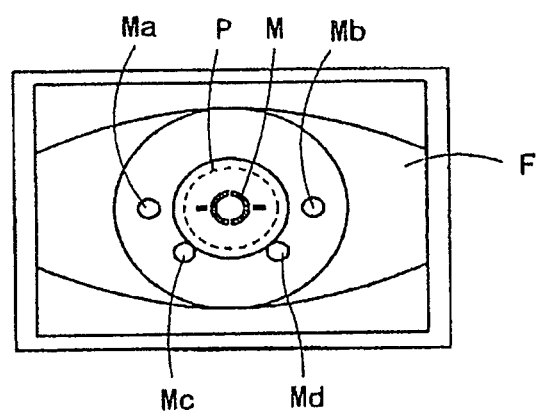
FIG. 3 is a view showing a display example of an anterior-segment image picked up by a two-dimensional image pickup element.

The anterior-segment observation optical system 60 includes a field lens 61, a mirror 62, a diaphragm 63, a relay lens 64, and a two-dimensional image pickup element 65 having sensitivity to an infrared range, which are arranged in a reflecting direction of the dichroic mirror 24. The image pickup element 65 doubles as image pickup means for alignment target detection, and picks up an image of an anterior segment of the eye E illuminated by the illumination light source 58 arranged to emit infrared light having a center wavelength of 940 nm and images of alignment targets. Illumination light emitted from the illumination light source 58 is reflected by the anterior segment, passes through the objective lens 25, the dichroic mirror 24, and the field lens 61 through the relay lens 64, and is photo-received on the image pickup element 65. By lighting of the light sources of the alignment target projection optical system 50, the alignment targets projected onto the anterior segment are photo-received on the image pickup element 65. Output of the image pickup element 65 is inputted to a control unit 80, and an anterior-segment image F picked up by the image pickup element 65 is displayed on the monitor 8, as shown in FIG. 3. The anterior-segment observation optical system 60 doubles as means for detecting an alignment state of the apparatus main body 3 with respect to the eye E.

Control System

Output of the image pickup elements 65, 38 and 35 is inputted to the control unit 80. The control unit 80 detects the alignment targets in the anterior-segment image picked up by the image pickup element 65, and detects an alignment deviation amount of the apparatus main body 3 with respect to the eye E based on a photo-receiving signal from the image pickup element 65. The control unit 80 detects and processes the focus target in the fundus image picked up by the image pickup element 38. The control unit 80 controls the image displayed on the monitor 8. When performing successive fluorescent photographing, the control unit 80 controls the light source 14 to perform successive light emission at given time intervals (i.e., the control unit 80 also functions as a light emission control unit), and controls the photographing unit 3 (the photographing optical system) to move with respect to the eye E based on a detection result of the alignment targets during a period of the successive light emission (i.e., the control unit 80 also functions as a movement control unit). The control unit 80 is connected with the XYZ driving unit 6, the moving mechanism 49, the inserting and removing mechanism 39, the inserting and removing mechanism 66, the inserting and removing mechanisms A and B, the rotation knob 4a, a photographing switch 4b, a counter switch 9, a switch unit 90 having various switches, a memory 85 as storage means, the light sources, and other constituent elements.

The switch unit 90 includes a switch 91 for selecting either of an automatic focus mode of automatically performing focusing on the fundus and a manual focus mode of manually performing focusing on the fundus, a focus adjustment switch 92 for manually performing focus adjustment, a photographing changing switch 93 for selecting either of a fundus photographing mode of performing color photographing of the fundus and a fluorescent photographing mode of performing fluorescent photographing of the fundus, a switch 94 for selecting either of an automatic photographing mode of automatically performing fundus photographing when photographing conditions are met and a manual photographing mode of performing fundus photographing each time the examiner presses the photographing switch 4b, and other switches. The counter switch 9 is arranged to count an elapsed time from intravenous injection of a fluorescent agent. By pressing the counter switch 9, a counter 9a is activated, and an elapsed time since the counter switch 9 is pressed is displayed on the monitor 8. When the automatic photographing mode is selected, the control unit 80 controls photographing operation based on a count signal from the counter 9a. In addition, the control unit 80 controls the monitor 8 to electrically generate and display a reticle mark M defining an alignment reference and a circular mark P indicating a minimum photographable pupil size at given positions on a screen of the monitor 8.

Descriptions of operations of the fundus camera having the configuration as described above will be given, mainly on operations of fluorescent photographing. In the following descriptions, the fundus camera is put in the fluorescent photographing mode by operation of the photographing changing switch 93 and in the automatic photographing mode by the switch 94. In this state, the exciter filter EX and the barrier filter BA are not on the optical paths.

First, the examiner drops a mydriatic agent on the examinee's eye to fully dilate the examinee's eye, and makes the face of the examinee supported by the face supporting unit 5. Then, the examinee is made to fixate a fixation lamp (not shown) (for example, the fixation lamp is disposed in front of the examinee's eye). In the initial stage, the dichroic mirror 24 is on the optical path of the photographing optical system 30 and the image of the anterior segment illuminated by the light source 58 is picked up by the image pickup element 65 and is displayed on the monitor 8. Then, the examiner moves the photographing unit 3 laterally and vertically by operation of the joystick 4 in order that the anterior-segment image may be displayed on the monitor 8. As shown in FIG. 3, when the anterior-segment image is displayed on the monitor 8, alignment target images Ma to Md are also displayed on the monitor 8.

When the alignment target images Ma to Md that are projected onto the cornea are detected by the image pickup element 65, the control unit 80 starts automatic alignment of automatically adjusting the position of the fundus photographing optical system 30b with respect to the examinee's eye based on the detection result of the alignment targets. During the automatic alignment, the control unit 80 takes an intermediate position between the target images Ma and Mb as a corneal vertex position, and detects an alignment state (a deviation amount) of the corneal vertex position that is obtained by the target images Ma and Mb with respect to an alignment reference position that is previously set on the image pickup element 65. Then, the control unit 80 performs alignment in the X and Y directions in order that the photographing unit 3 may be positioned within a given alignment allowable range based on a detection result of the alignment state. In addition, the control unit 80 detects the alignment state in the Z direction by comparing the distance between the target images Ma and Mb formed by infinite light and the distance between the target images Mc and Md formed by finite light, and performs alignment of the photographing unit 3 in the Z direction (for details, see Japanese Patent Application Laid-open Publication No. H06-046999 corresponding to U.S. Pat. No. 5,463,430).

When the alignment of the photographing unit 3 with the eye E is completed, the control unit 80 detects the focus target in the fundus image picked up by the image pickup element 38 and performs focus adjustment by moving the focusing lens 32 and the focus target projection optical system 40 in the optical axis direction based on a detection result (hereinafter, simply referred to as automatic focus adjustment).

After the completion of alignment and automatic focus adjustment, the examiner administers intravenous injection of a fluorescent agent (e.g., fluorescent sodium) to the examinee and presses the counter switch 9. When the counter switch 9 is pressed, the control unit 80 controls the counter 9a to count a fluorescent time and inserts the exciter filter EX and the barrier filter BA into the optical paths. In addition, the control unit 80 turns the light source 41 off and stops automatic focus adjustment. It should be noted that automatic alignment is maintained during fluorescent photographing. The counter 9a outputs a clock signal at given time intervals Δt (e.g., one-second intervals) and controls the timing of fluorescent photographing and the photographing period based on the clock signal.

Figure 4:
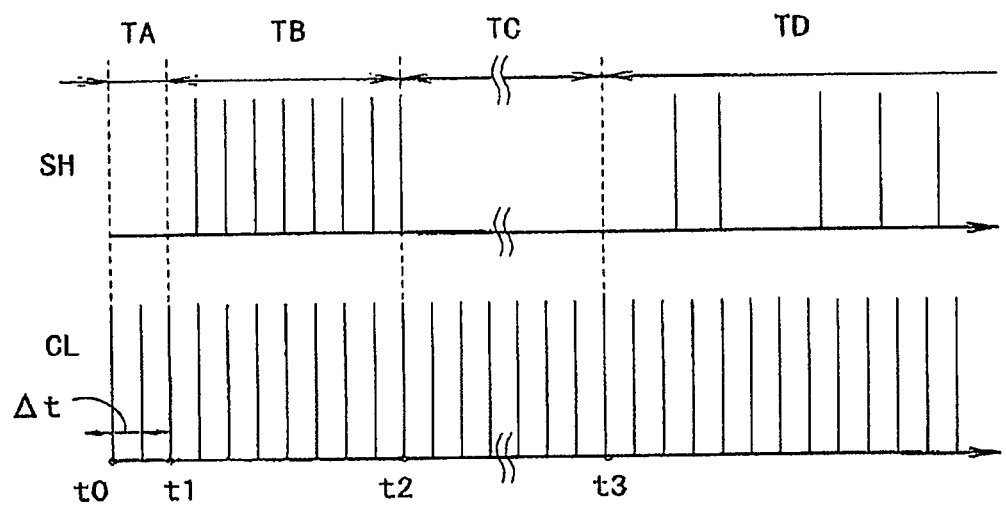
FIG. 4 is a view for explaining a relation between the timing of fluorescent photographing and a clock signal.

Hereinafter, a description of control of operations during fluorescent photographing will be provided based on a relation between the timing of fluorescent photographing and the clock signal outputted from the counter 9a referring to FIG. 4. In FIG. 4, the upper section indicates timing SH of fluorescent photographing and the lower section indicates timing CL of output of the clock signal from the counter 9a.

A period TA indicates a period of time from the injection of the fluorescent agent to appearance of the fluorescent agent in the fundus (about eight to fifteen seconds). Because the counter switch 9 is pressed immediately after the injection of the fluorescent agent, the timing of starting the count of the fluorescent time is substantially the same as the timing of the injection of the fluorescent agent. A period TB is a period of time in which the fluorescent agent is initially circulated once in the fundus (about twenty to thirty seconds later after the injection). In the period TB, choroidal and retinal vessels are favorably observed, and successive fluorescent photographing is performed. A period TC is a non-operating period of time in which the fluorescent agent is circulated in the body of the examinee. A period TD is a period of time in which the fluorescent agent appears again in the fundus (about 10 to 40 minutes later after the injection). Abnormal function (a blood-retina barrier) can be observed in a fluorescent image photographed in the period TD.

A time t1 indicating the timing of switching the period TA to the period TB (the starting time of successive fluorescent photographing) and a time t2 indicating the timing of switching the period TB to the period TC (the ending time of successive fluorescent photographing) are previously stored in the memory 85. The times t1 and t2 are detected based on the clock signal, and the control unit 80 starts and ends successive fluorescent photographing at the times t1 and t2.

In the period TA, the control unit 80 performs only automatic alignment and does not perform automatic photographing. When the control unit 80 detects that the time reaches the period TB in which the fluorescent agent starts to appear at the fundus based on the clock signal from the counter 9a, the control unit 80 controls the light source 14 to perform light emission in synchronization with the clock signal from the counter 9a so as to perform successive fluorescent photographing.

When the clock signal is detected in the period TB, the control unit 80 controls the light source 14 to perform light emission and drives the inserting and removing mechanisms 66 and 39 to momentarily remove the pop-up mirrors 24 and 34 from the optical paths. The visible light from the light source 14 is limited to blue light defining fluorescent excitation light by the exciter filter EX and travels the optical path as described above to illuminate the fundus. The excitation light reflected from the fundus is completely cut by the barrier filter BA. The fluorescent agent circulating in blood vessels of the fundus is excited by the excitation light to emit fluorescent light having a wavelength of more than 520 nm. The fluorescent light passes through the objective lens 25, the apertured mirror 22, the diaphragm 31, and the barrier filter BA. Then, the fluorescent light passes through the focusing lens 33 to form an image on an image pickup surface of the image pickup element 35, by which fluorescein fundus angiography by the fluorescent light is photographed. The photographed fluorescein fundus angiography (the fluorescent image) is stored in the memory 85 and is successively updated and displayed on the monitor 8. Accordingly, a change of the fluorescent image during successive fluorescent photographing in the initial fluorescent period can be easily checked. In addition, upon completion of initial photographing, the pop-up mirrors 24 and 34 are inserted into the optical paths. During successive fluorescent photographing, the pop-up mirrors 24 and 34 are inserted and removed in synchronization with the photographing operation, and in the state that the pop-up mirror 24 is disposed on the optical path, the control unit 80 activates automatic alignment using the anterior-segment observation optical system 60 so as to prevent the alignment deviation during successive fluorescent photographing.

As described above, in the period TB, light emission of the light source 14 and removal of the pop-up mirrors 24 and 34 from the optical paths are repeatedly performed based on the clock signal at the preset timing of photographing, and automatic alignment is performed, so that a plurality of fluorescent images with no positional deviation are obtained.

In the preferred embodiment of the present invention, automatic alignment is performed during photographing in the period TB. However, if the alignment is not completed before subsequent photographing timing, the control unit 80 gives a high priority to the alignment and cancels photographing by the photographing optical system 30b (light emission of the light source 14). After then, based on a signal indicating that the alignment is in the allowable range, photographing by the photographing optical system 30b is performed in synchronization with a subsequent clock signal.

When the control unit 80 detects that the time reaches the time t2 (the period TC) based on the clock signal, the control unit 80 drives the inserting and removing mechanisms A and B to remove the exciter filter EX and the barrier filter BA from the optical paths. In addition, the control unit 80 ends the automatic photographing mode when the time reaches the time t2 (the period TC) and controls the monitor 8 to display as such. In other words, in the period TC or later, the manual photographing mode is established in which each time the examiner presses the photographing switch 4b, single fluorescent photographing is performed. In the period TC in which the fluorescent agent from the fundus circulates in the body, the examiner makes the examinee take his/her face off from the face supporting unit 5 and have a break.

When the time reaches the period TD (the time t3) in which the fluorescent agent appears again in the whole fundus, if fluorescent photographing is to be performed, the examiner makes the face of the examinee supported by the face supporting unit 5 and makes the examinee fixate a fixation lamp not shown. Then, the examiner presses the photographing switch 4b to photograph a necessary portion of the eye. At this time, the inserting and removing mechanisms A and B are driven in synchronization with a trigger signal from the photographing switch 4b, and the exciter filter EX and the barrier filter BA are inserted into the optical paths. In addition, light emission of the light source 14 is performed, and the inserting and removing mechanisms 39 and 66 are driven to momentarily remove the pop-up mirrors 24 and 34 from the optical paths.

When the secondary fluorescent photographing is performed in the period TD, automatic alignment of the photographing unit 3 with respect to the eye E is constantly performed by the anterior-segment observation optical system 60, and accordingly, more accurate fluorescent photographing can be performed. In the manual photographing mode, the clock only has the function of making the monitor 8 display the elapsed time, and the timing of fluorescent photographing and the timing of insertion and removal of the filters are provided by pressing the photographing switch 4b. Also in the manual photographing mode, light emission of the light source 14 is performed at predetermined time intervals (e.g., at one-second intervals) during the time when the photographing switch 4b is pressed, and successive fluorescent photographing is performed. Also in the manual photographing mode, automatic alignment is performed during photographing.

In the descriptions provided above, automatic focus adjustment is deactivated. However, the present invention is not limited thereto, and automatic focus adjustment may be activated. In the case of automatic focus adjustment, the barrier filter BA is imparted with the function of transmitting infrared light and fluorescent light. Accordingly, even though the barrier filter BA is disposed on the optical path during successive photographing, the focus target projected onto the fundus is transmitted by the barrier filter BA and is photo-received on the image pickup element 38. Also in the case of performing both of automatic alignment and automatic focus adjustment during successive photographing, similar to the case of performing only automatic alignment, light emission of the light source 14 is performed in synchronization with the clock signal from the counter 9a during successive photographing so as to perform fundus photographing, and then automatic alignment and automatic focus adjustment are performed during a period up to the subsequent clock signal.

The time before alignment completion in the case of performing both of automatic alignment and automatic focus adjustment is longer than the case of performing only automatic alignment, which could exert an effect on successive fluorescent photographing. In such a case, an allowable range of focus completion is expanded more than the allowable range of focus completion in normal fundus photographing.

In addition, settings of the times t1 and t2 of the period TB in which successive photographing is performed may be changeable. For example, input means for changing the timing of photographing may be provided to the switch unit 90. With the means, the starting time and ending time of successive photographing can be changed in consideration of the experience of the examiner or the age or symptom of the examinee, and fluorescent photographing can be performed under more favorable conditions.

In the preferred embodiment of the present invention, the fluorescent image is displayed on the monitor 8 of the fundus camera 3. However, the present invention is not limited thereto. For example, it is also preferable that a fundus photographing apparatus in which a fundus camera and a personal computer (PC) are connected to each other and a fundus image is managed on the PC is used, and a fluorescent image obtained by fluorescent photographing is transferred to the PC and is successively displayed on a monitor (display) of the PC.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications is suited to the particular use contemplated. It is intended that the scope of the invention be defined by the claims appended hereto, and their equivalents.

What is claimed is:

1. A fundus photographing apparatus arranged to perform fluorescent photographing by projecting flash light for fluorescent excitation onto an examinee's eye, the apparatus comprising:

a photographing optical system comprising a focusing lens movable in an optical axis direction and arranged to photograph a fundus of the eye illuminated by photographing illumination light;

an alignment detection optical system arranged to photo-receive by a first image pickup element an alignment target projected onto the eye by an alignment target projection optical system and detect an alignment state of the photographing optical system with respect to the eye based on a photo-receiving result by the first image pickup element;

a focus detection optical system arranged to photo-receive by a second image pickup element a focus target projected onto the fundus by a focus target projection optical system and detect a focus state of the fundus adjusted by movement of the focusing lens based on a photo-receiving result by the second image pickup element;

a light emission control unit arranged to control a light source to perform successive light emission of the flash light for fluorescent excitation at predetermined time intervals in a predetermined period in order to perform fluorescent photographing; and a movement control unit arranged to perform movement control of the photographing optical system with respect to the eye in an automatic manner based on a detection result obtained by the alignment detection optical system during the predetermined period of the successive light emission by the light emission control unit.

2. The fundus photographing apparatus according to claim 1, wherein in the predetermined period of the successive light emission, the movement control unit is arranged to stop movement control of the focusing lens based on a detection result by the focus detection optical system.

3. The fundus photographing apparatus according to claim 2, further comprising a counter arranged to count an elapsed time from introduction of a fluorescent agent and output a clock signal at predetermined time intervals, wherein
the light emission control unit is arranged to perform the light emission control of the light source based on the clock signal from the counter and perform the movement control of the focusing lens based on the clock signal from the counter.

4. The fundus photographing apparatus according to claim 3, wherein after a lapse of a predetermined time from start of the time counting, the light emission control unit performs the successive light emission control based on the clock signal from the counter for a predetermined period, and after the period of the successive light emission, the light emission control unit performs the light emission control of the light source based on a trigger signal from a photographing switch.

5. The fundus photographing apparatus according to claim 4, wherein a portion of an optical path of the alignment detection optical system and a portion of an optical path of the photographing optical system are made common by a mirror, the mirror is insertably and removably disposed on the optical paths, and the alignment detection is performed when the mirror is disposed on the optical paths in the period of the successive light emission by the light emission control unit.

6. The fundus photographing apparatus according to claim 5, wherein in the period of the successive light emission, when the movement control of the photographing optical system by the movement control unit is not completed before subsequent light emission timing, the light emission control unit gives a high priority to the movement control by the movement control unit and cancels the light emission of the light source in synchronization with the clock signal.

7. The fundus photographing apparatus according to claim 6, wherein after cancelling the light emission in the period of the successive light emission, the light emission control unit controls the light source to perform the light emission in synchronization with a subsequent clock signal in response to a signal indicating completion of the movement control by the movement control unit.

8. The fundus photographing apparatus according to claim 7, further comprising:
a monitor arranged to display a fundus image;
a fundus observation optical system comprising an image pickup element having sensitivity to an infrared range and arranged to observe the fundus, and a fundus photographing optical system comprising an image pickup element having sensitivity to a visible range and arranged to photograph the fundus, the optical systems defining the photographing optical system; and
a control unit arranged to control the monitor to display in real time an infrared fundus image obtained in the fundus observation optical system before the successive light emission, and control the monitor to successively display a fluorescent fundus image obtained in the fundus photographing optical system during the successive light emission.

9. A fundus photographing apparatus arranged to perform fluorescent photographing by projecting excitation light for fluorescent photographing onto an examinee's eye, the apparatus comprising:
a photographing optical system arranged to photograph a fundus of the eye;
an alignment detection optical system arranged to detect an alignment state of the photographing optical system with respect to the eye;
a focus detection optical system arranged to detect a focus state of the photographing optical system with respect to the fundus;
a light emission control unit arranged to control a light source to perform successive emission of the excitation light; and
a movement control unit arranged to perform movement control of the photraphing optical system with respect to the eye in an automatic manner based on a detection result obtained by the alignment detection optical system during the successive emission of the excitation light by the light emission control unit.

10. The fundus photographing apparatus according to claim 9, wherein the movement control unit is arranged to stop movement control of a focusing lens in the photographing optical system based on a detection result by the focus detection optical system during the successive emission of the excitation light.

* * * * *